United States Patent
Kim

(10) Patent No.: US 8,899,983 B2
(45) Date of Patent: Dec. 2, 2014

(54) METHOD AND APPARATUS FOR PREPARING DENTURE

(75) Inventor: Tae Hyung Kim, La Canada, CA (US)

(73) Assignee: Dentca, Inc., Los Angeles, CA (US)

(*) Notice: Subject to any disclaimer, the term of this patent is extended or adjusted under 35 U.S.C. 154(b) by 0 days.

(21) Appl. No.: 13/598,413

(22) Filed: Aug. 29, 2012

(65) Prior Publication Data
US 2012/0322031 A1 Dec. 20, 2012

Related U.S. Application Data

(63) Continuation of application No. 12/782,663, filed on May 18, 2010, now Pat. No. 8,277,216.

(60) Provisional application No. 61/179,698, filed on May 19, 2009.

(51) Int. Cl.
*A61C 9/00* (2006.01)
*A61C 19/05* (2006.01)

(52) U.S. Cl.
CPC .............. *A61C 9/0006* (2013.01); *A61C 19/05* (2013.01)
USPC ........................................... 433/214; 433/37

(58) Field of Classification Search
CPC ......... A61C 9/00; A61C 9/0006; A61C 9/004
USPC ......... 433/34, 37, 68, 69, 214, 35, 36, 38–40, 433/41–45, 70, 71, 215
See application file for complete search history.

(56) References Cited

U.S. PATENT DOCUMENTS

| 310,407 | A | * | 1/1885 | Garner ............................ 433/45 |
| 3,626,594 | A | | 12/1971 | Zinner et al. |
| 3,890,711 | A | | 6/1975 | Burns |
| 4,145,812 | A | | 3/1979 | Johnson et al. |
| 4,543,062 | A | | 9/1985 | Lee |
| 4,657,509 | A | | 4/1987 | Morris |
| 4,789,334 | A | | 12/1988 | Wedenig et al. |

(Continued)

FOREIGN PATENT DOCUMENTS

| JP | 33-17491 | 10/1958 |
| JP | 11-318956 | 11/1999 |

(Continued)

OTHER PUBLICATIONS

United States Patent and Trademark Office U.S. Appl. No. 12/782,663, Advisory Action dated Jun. 6, 2012, 3 pages.

*Primary Examiner* — Cris L Rodriguez
*Assistant Examiner* — Matthew Seward
(74) *Attorney, Agent, or Firm* — Lee, Hong, Degerman, Kang & Waimey

(57) ABSTRACT

A dental impression tray assembly includes an upper tray and a lower tray operable with the upper tray, and the lower tray includes a first piece configured to measure jaw relations of a patient's mouth and a pair of second pieces detachably attachable to the first piece. The first piece of the lower tray is inserted into the patient's mouth independently of the pair of second pieces of the lower tray to measure the jaw relations and to obtain a bite registration. After the first piece is connected to the pair of second pieces, the assembly allows a final gum impression of the patient's lower gum to be obtained.

17 Claims, 6 Drawing Sheets

(56) References Cited

U.S. PATENT DOCUMENTS

| | | | |
|---|---|---|---|
| 5,186,624 A | | 2/1993 | Gottsleben |
| 5,722,828 A | * | 3/1998 | Halstrom .................. 433/69 |
| 6,196,840 B1 | | 3/2001 | Zentz et al. |
| 6,231,339 B1 | * | 5/2001 | Skarky ..................... 433/71 |
| 8,070,489 B2 | * | 12/2011 | Massad ..................... 433/71 |
| 2003/0180681 A1 | | 9/2003 | Kwon et al. |
| 2007/0190492 A1 | * | 8/2007 | Schmitt .................... 433/213 |
| 2008/0254406 A1 | | 10/2008 | Wagner |

FOREIGN PATENT DOCUMENTS

| | | |
|---|---|---|
| JP | 2006-192223 | 7/2006 |
| JP | 2009-517144 | 4/2009 |
| KR | 10-2009-0036643 | 4/2009 |
| WO | 02-00134 | 1/2002 |
| WO | 2008/083857 | 7/2008 |

* cited by examiner

METHOD AND APPARATUS FOR PREPARING DENTURE

CROSS REFERENCE TO RELATED APPLICATIONS

This application is a continuation of U.S. patent application Ser. No. 12/782,663, filed on May 18, 2010, now U.S. Pat. No. 8,277,216, which claims the benefit of Provisional Application No. 61/179,698 filed on May 19, 2009, the contents of which are all hereby incorporated by reference herein in their entirety.

FIELD OF THE INVENTION

The present disclosure relates generally to dentures, and more particularly to a simplified method and apparatus for fabricating dentures. In particular, the present invention is directed to reducing a number of visits required for fabrication of a denture without compromising the quality of the denture by using the inventive method and apparatus.

DESCRIPTION OF THE RELATED ART

Complete dentures are constructed to replace missing teeth for patients who are fully edentulous. Fabrication of a set of complete dentures is a challenging task for any dentist. Complete dentures should be comfortable when inserted into the mouth of a patient. Therefore, impressions of edentulous patients must be accurate, duplicating all the details of the oral tissues. Imperfection in the impression affects the fit of the dentures, and thus, may cause serious effects when wearing the dentures.

Dentures are conventionally constructed and fitted by dentists with the assistance of dental technicians using a flask investment technique. This complex process requires measurements of masticatory function, impressions of the gum and surrounding tissues of the affected area, study models and working models, and a series of back and forth steps between the dentist and the dental technician to manufacture the denture. The entire process of constructing dentures using conventional methods and devices requires a number of appointments between the dentist and the patient, and involves a significant amount of time and skill.

Generally, a patient must make a plurality of visits to a dentist to make a set of dentures. Such visits are necessary in order for a dentist to take an impression of the patient's gums, as well as a bite registration of the patient's jaw position and vertical dimension.

For example, during a first visit, a dentist examines a patient and takes a preliminary alginate impression of the patient using stock trays. After the preliminary alginate impression is taken on the impression material, the impression tray is delivered to a laboratory. In the laboratory, plaster is poured onto the preliminary alginate impression to form accurate models of the shape of the edentulous ridges. The preliminary alginate impression is used to make custom fitting impression trays for a final impression.

During a second visit, the dentist checks and adjusts the custom fitting impression trays as necessary and takes the final impression. Afterwards, in the laboratory, a master model is created and a base plate is fabricated based on the final impression received from the dentist. Then, a bite registration rim or block, usually made of wax, is fabricated from the master gum mold. The master gum mold, with the bite registration rim attached thereto, is sent back to the dentist.

During a third visit, the bite registration rim is inserted into the mouth of the patient, and adjusted inside the mouth to determine maxilla-mandibular relations and to take a bite registration. Further, artificial teeth to be used for the denture are selected by the dentist and the patient. The adjusted bite registration rim is sent back to the laboratory to fabricate a wax try-in. The laboratory returns the wax try-in with the actual final teeth lined up along the outer edge of the wax rim. The wax try-in looks similar to a real denture except that the base fits loosely on the gums and the teeth are embedded in wax instead of plastic.

During a fourth visit, the dentist examines how the wax try-in looks and works in the patient, checking occlusal and vertical dimension. If adjustments are necessary, the wax try-in can be sent back to the laboratory to reset the teeth. If no adjustments are needed, the wax try-in is sent back to the laboratory to be processed and finished. In the laboratory, the existing base and wax are discarded, and replaced by a tightly fitting plastic denture base.

During a fifth visit, the finished denture is then inserted into the mouth of the patient and adjusted as needed. The denture is also checked for occlusion and corrected, if necessary. As discussed above, it may generally take at least four or more visits of a patient until the finished dentures are finally inserted into the mouth of the patient. Thus, the multi-step process of preparing a set of dentures, requiring several iterations between the dentist and the dental laboratory is time-consuming, labor intensive and costly.

Moreover, difficulties exist in producing a good quality denture due to the great diversity in sizes and shapes of patients' mouths, and facial features requiring custom fabrication of each denture. Thus, standardization of prefabricated dentures is very difficult. Proposals to overcome the shortcomings of the conventional methods, such as multiple visits, intensive labor, and laboratory time needed for the fabrication of dentures, have had little success.

The shortcomings of prior proposals to overcome some of the difficulties in producing a conventional custom denture include: (1) Difficulty in collecting all necessary data to fabricate a high quality denture during one visit using the conventional method; (2) Difficulty in taking an impression and measuring jaw relations together in the conventional tray; (3) Expense, complexity and length of the procedure; (4) Skill level required; (5) Poor fit to the bite of an individual patient; (6) Excessive thickness or thinness of the denture base; (7) Use of articulated models, plaster and wax; (8) Poor fit to the tissue area of an individual patient; and (9) Poor functionality. Therefore, there is a need for a method and apparatus that will reduce the length of the procedure, and the number of times the patient visits the dentist for fabrication of a denture while providing a perfect fit of the denture to the patient.

SUMMARY OF THE INVENTION

The present invention overcomes all of the aforementioned shortcomings by providing a dental device that is convenient for a health professional to manipulate and software that allows accurate manufacturing of a complete denture without intensive manual labor. The present invention reduces the number of patient visits, cost and time conventionally required to produce a custom denture.

In accordance with one embodiment of the present invention, a dental impression tray assembly includes an upper tray and a lower tray operable with the upper tray, the lower tray including a first piece configured to measure jaw relations of a patient's mouth and a pair of second pieces detachably attachable to the first piece, wherein the first piece is inserted into the patient's mouth independently of the pair of second pieces to measure the jaw relations and to obtain a bite registration, and wherein the assembly is configured to allow a final gum impression of the patient's lower gum to be obtained after the first piece is connected to the pair of second pieces.

In accordance with another embodiment of the present invention, a method of measuring jaw relations and a final gum impression of a patient's mouth during a patient's single visit to a dentist using a dental impression tray assembly including a lower tray and an upper tray to fabricate a denture includes inserting a first piece of the lower tray into the patient's mouth, measuring the jaw relations using the first piece, attaching a pair of second pieces of the lower tray to the first piece after measuring the jaw relations, inserting the assembled first piece and the pair of second pieces into the patient's mouth, and obtaining the final gum impression of the patient's mouth.

These and other embodiments will also become readily apparent to those skilled in the art from the following detailed description of the embodiments having reference to the attached figures, the invention not being limited to any particular embodiment disclose.

BRIEF DESCRIPTION OF THE DRAWINGS

The above and other aspects, features, and advantages of the present invention will become more apparent upon consideration of the following description of preferred embodiments, taken in conjunction with the accompanying drawings.

DETAILED DESCRIPTION OF PREFERRED EMBODIMENTS

In the following detailed description, reference is made to the accompanying drawing figures which form a part hereof, and which show by way of illustration specific embodiments of the invention. It is to be understood by those of ordinary skill in this technological field that other embodiments may be utilized, and structural, electrical, as well as procedural changes may be made without departing from the scope of the present invention. Wherever possible, the same reference numbers will be used throughout the drawings to refer to the same or similar parts.

Figure 1A:
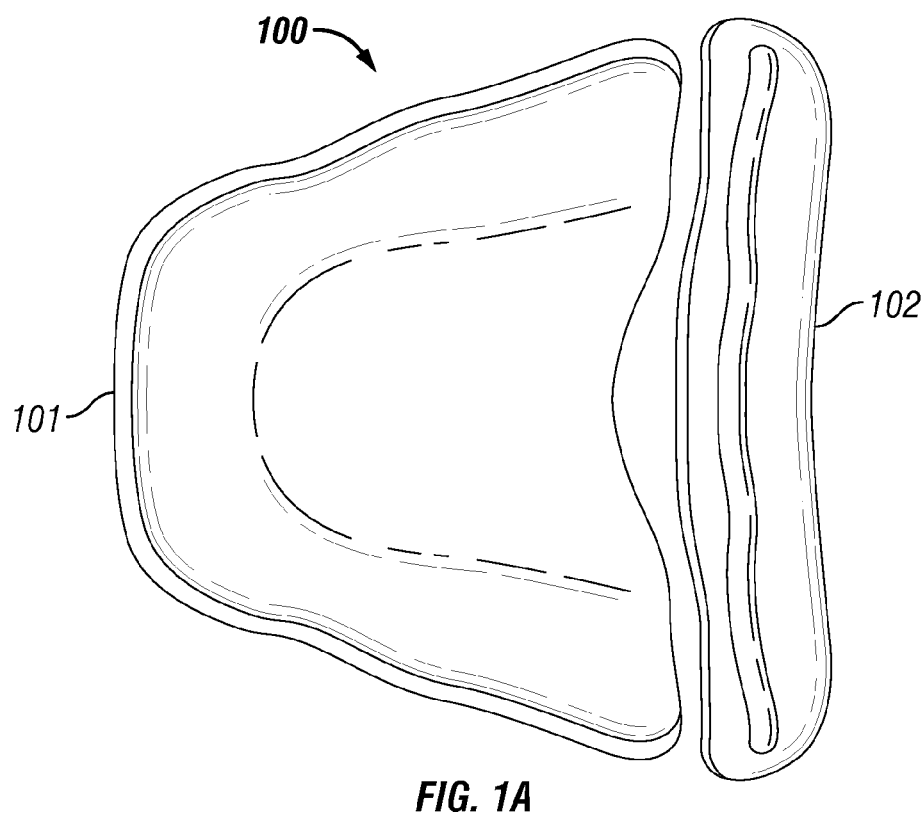
FIG. 1A is a top view of an upper tray according to an embodiment of the present invention, the upper tray comprising a first center piece and an outer piece where the first center piece and the outer piece are separated.
Figure 1B:
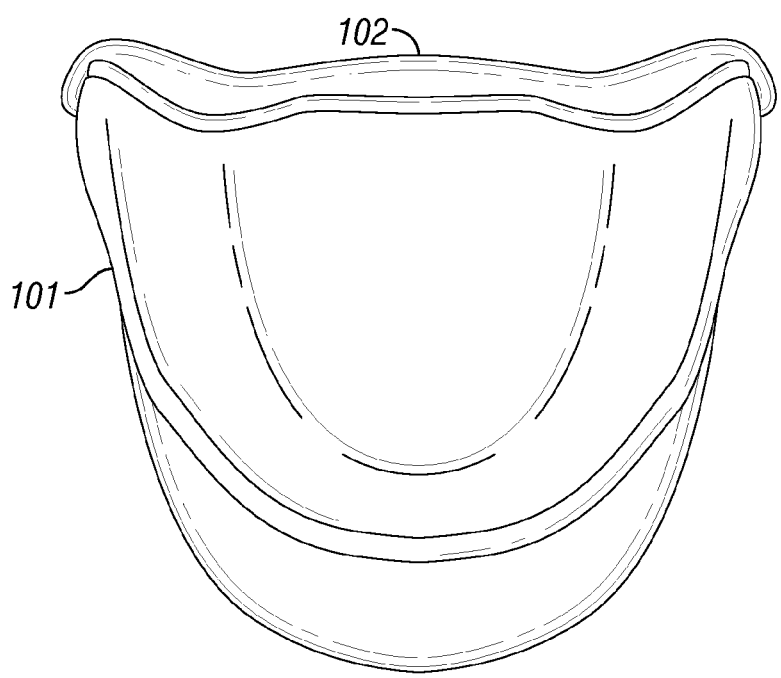
FIG. 1B is a top view of the upper tray where the first center piece and the outer piece are combined.
Figure 1C:
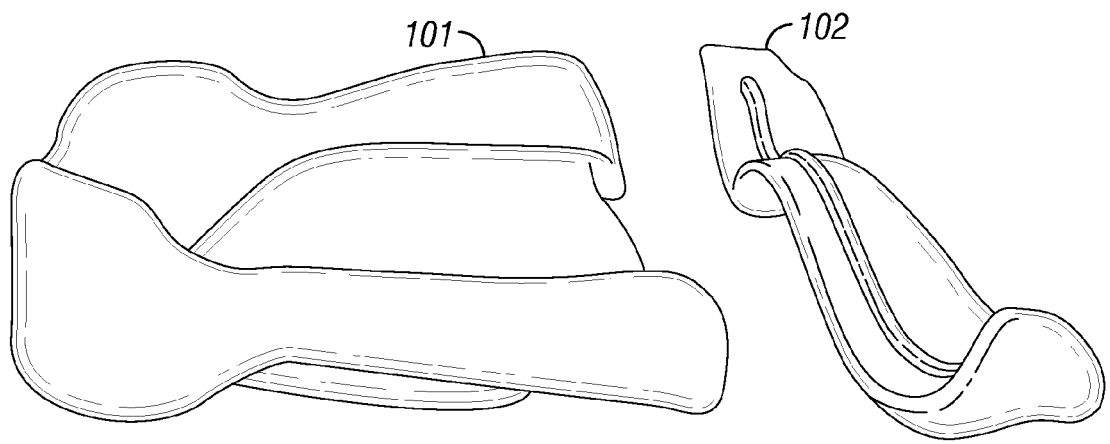
FIG. 1C is a disassembled perspective view of the upper tray.
Figure 1D:
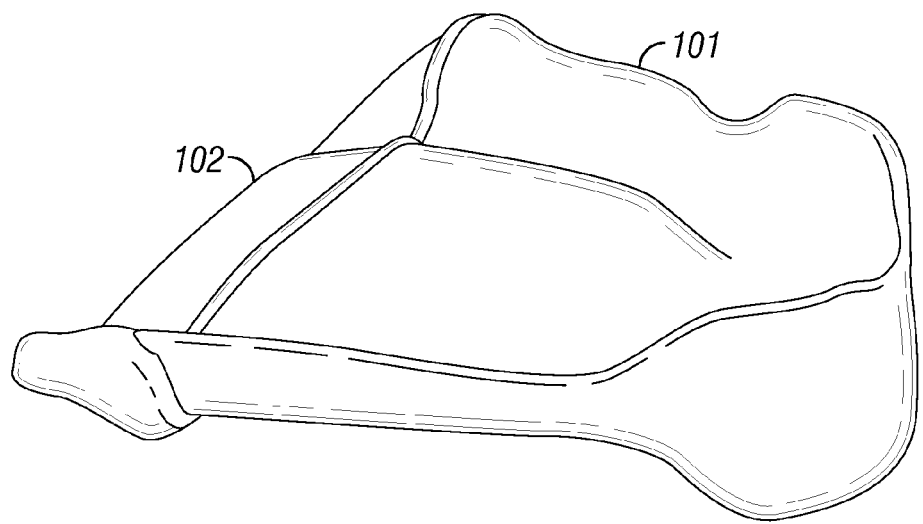
FIG. 1D is an assembled perspective view of the upper tray.
Figure 2A:
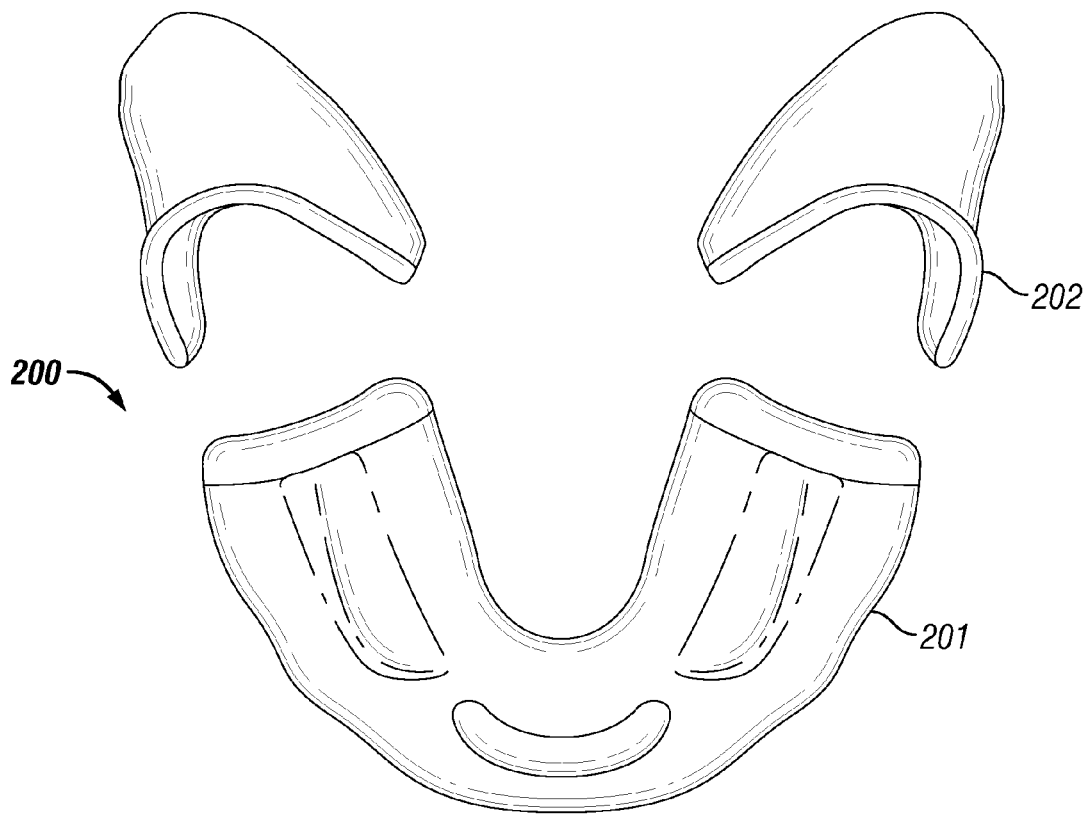
FIG. 2A is a top view of a lower tray according to an embodiment of the present invention, the lower tray comprising a second center piece and a pair of back pieces where the second center piece and the pair of back pieces are separated.
Figure 2B:
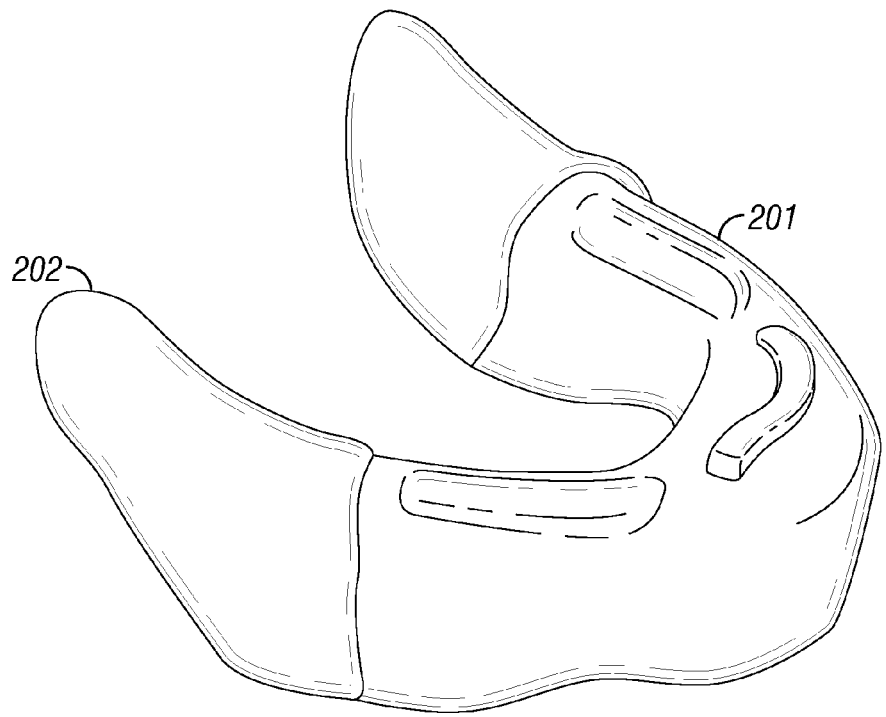
FIG. 2B is a perspective view of the lower tray in which the second center piece and the pair of back pieces are assembled.
Figure 2C:
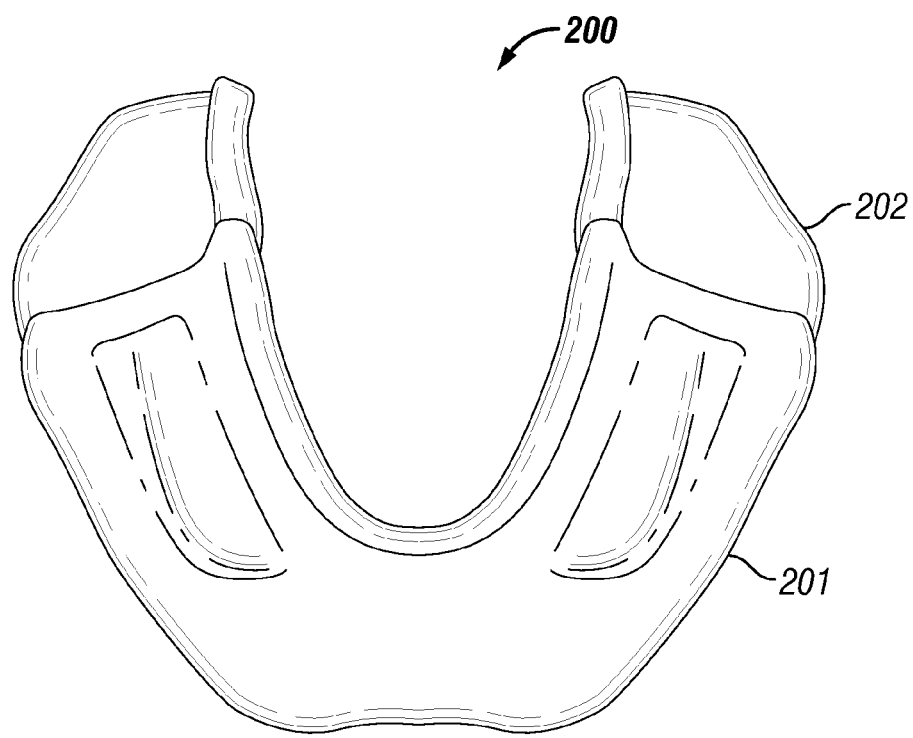
FIG. 2C is a bottom view of the lower tray in which the second center piece and the pair of back pieces are assembled.

According to an embodiment of the present invention, the inventive set of trays, including an upper tray 100 and a lower tray 200, are capable of measuring jaw relations and taking a final impression in a single visit. The set of trays 100 and 200 may be made of plastic and may be available in various sizes to accommodate different sizes of jaws. The set of trays 100 and 200 may include a plurality of pieces or portions that can be assembled or disassembled. The upper tray 100 may be formed as a single piece rather than two pieces 101 and 102 as shown in FIGS. 1A-1D. The lower tray 200 comprises a plurality of pieces 201 and 202 as shown in FIGS. 2A-2B to be accommodated in a mouth of a patient.

A first center piece 101 of the upper tray 100 and a second center piece 201 of the lower tray 200, as shown in FIGS. 1A-1D and FIGS. 2A-2B, respectively, are used to take jaw relations, such as a vertical dimension (VD) and a centric relation (CR). For example, the first and second center pieces 101 and 201 receive a polymer material and the first and second center pieces retaining the polymer material are individually inserted into the mouth to obtain a first impression or a partial impression of a patient's gum including about two-thirds of the gums including the anterior gums. If the upper tray 100 is formed of only a single piece, the final impression of the upper gum may be obtained at once, the first impression becoming the final impression for the upper gum.

Figure 3A:
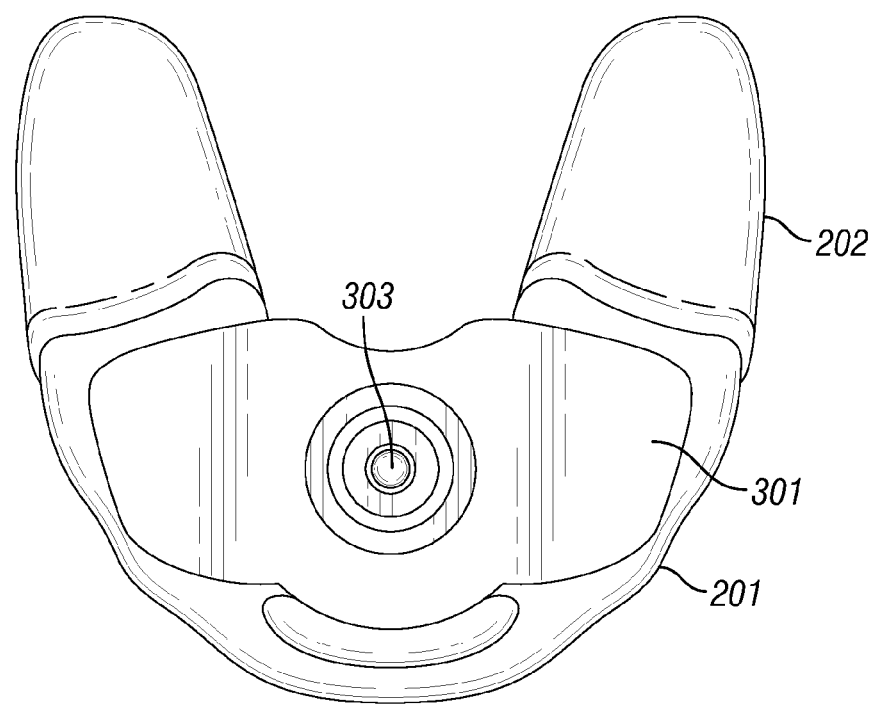
FIG. 3A is a top view of the assembled lower tray to which an intra-oral tracer is attached according to an embodiment of the present invention.
Figure 3B:
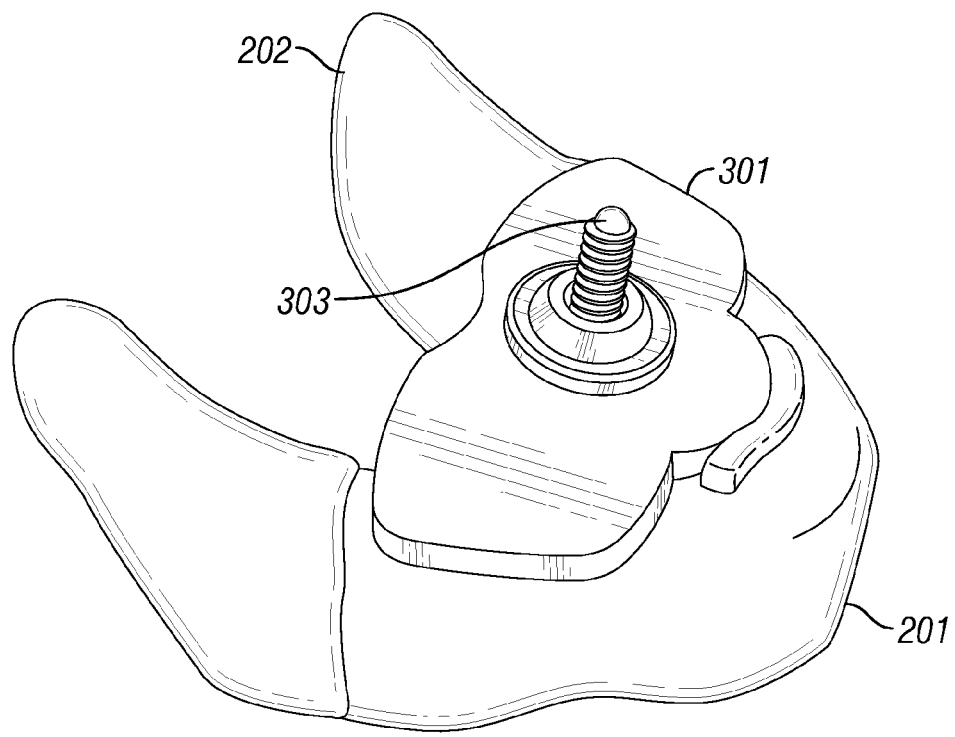
FIG. 3B is a perspective view of the assembled lower tray to which the intra-oral tracer is attached.
Figure 4:
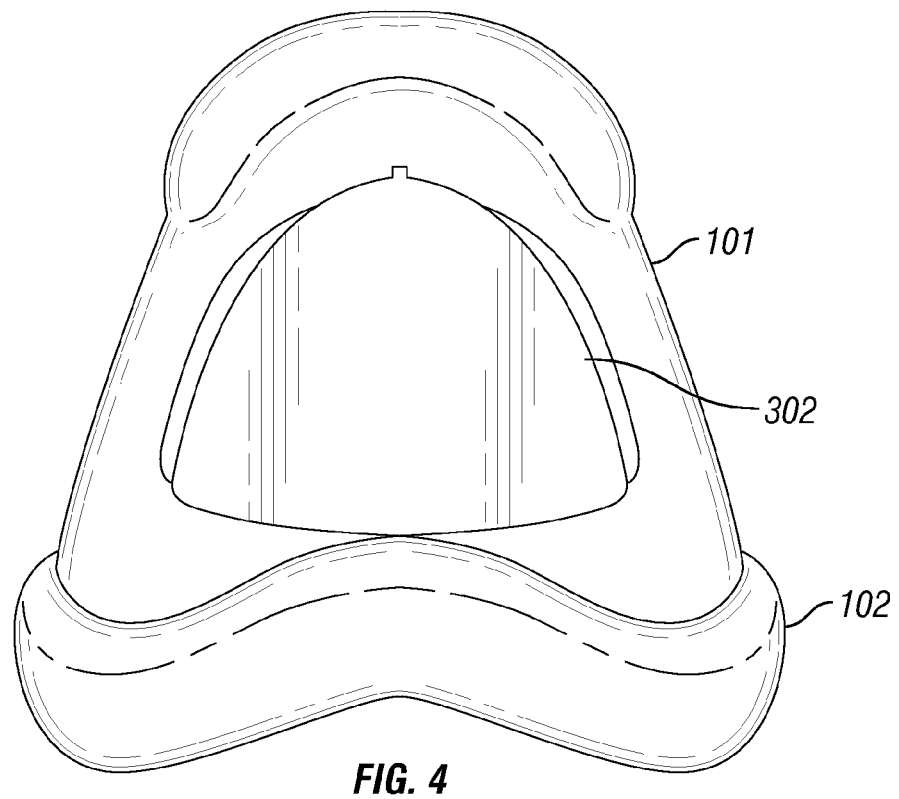
FIG. 4 is a bottom view of the assembled upper tray to which a cover to be contacted by the intra-oral tracer is attached.
Figure 5A:
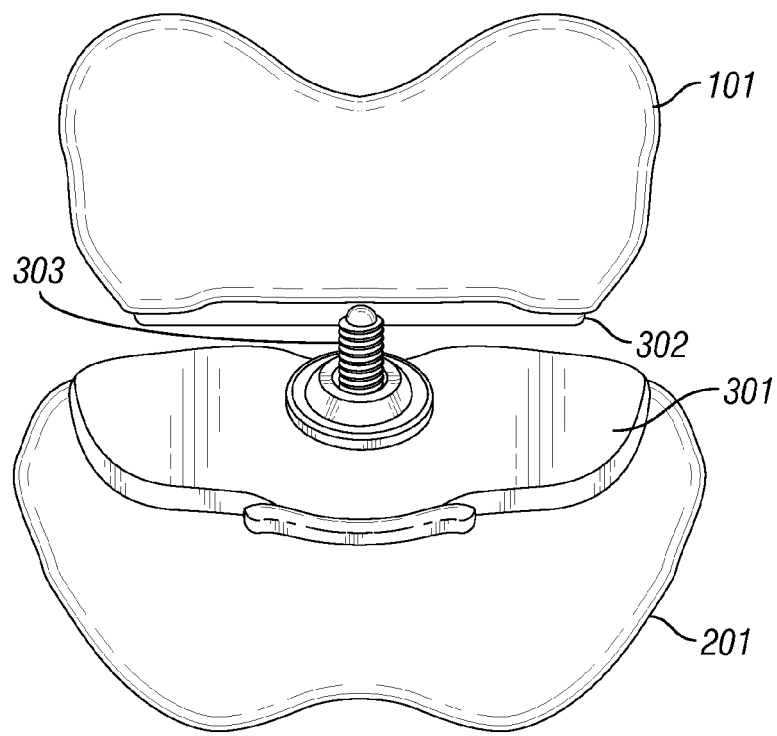
FIG. 5A is a frontal view of the first center piece of the upper tray with the cover and the second center piece of the lower tray with the intra-oral tracer, the intra-oral tracer contacting the cover.
Figure 5B:
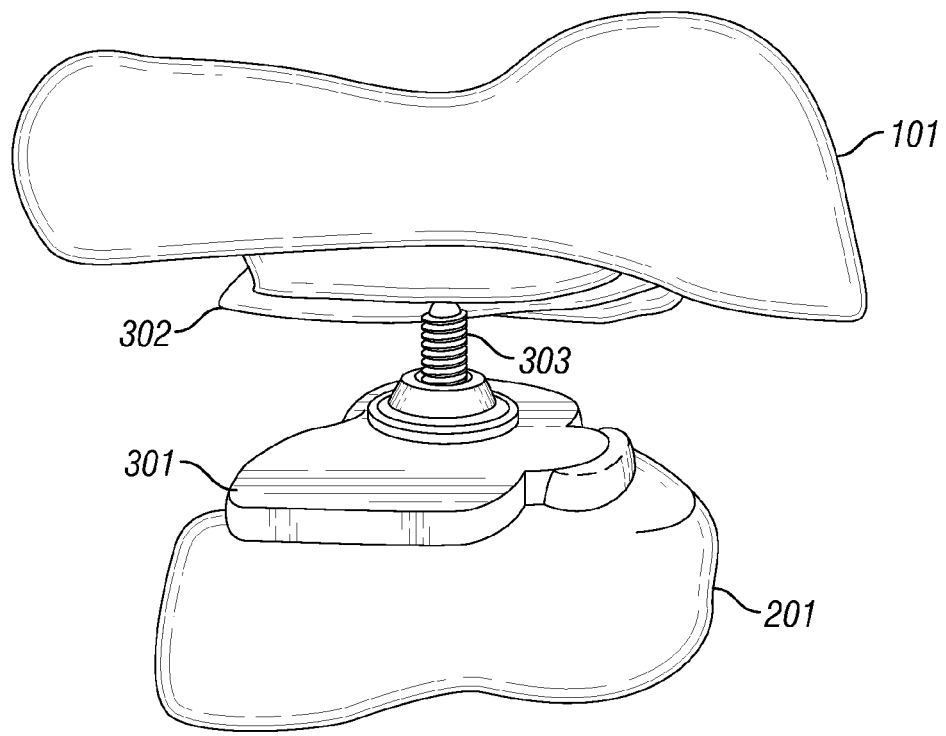
FIG. 5B is a side view of the first center piece of the upper tray with the cover and the second center piece of the lower tray with the intra-oral tracer, the intra-oral tracer contacting the cover.

Once the first impression is obtained, the first and second center pieces 101 and 201 retaining the partial impression are inserted into the mouth together with an intra-oral tracer 301 placed between the first center piece 101 and second center piece 201 as shown in FIGS. 5A and 5B. For example, the intra-oral tracer 301 may be inserted into an upper surface of the second center piece 201 of the lower tray 200 as shown in FIGS. 3A and 3B and a cover 302 may be placed on a lower surface of the first center piece 101 of the upper tray 100 as shown in FIG. 4. The upper piece 100 and the lower piece 200, as shown in FIGS. 5A and 5B, are inserted into the mouth together to measure jaw relations. When the upper tray 100 and the lower tray 200 are inserted into the mouth, the outer piece 102 and the pair of back pieces 202 are not attached to the first center piece 101 and the second center piece 201, respectively. Jaw relations are measured by lowering or raising the screw 303 of the intra-oral tracer 301 in the mouth to contact the cover 302. Once the intra-oral tracer 301 is adjusted to be in a clinically acceptable position, a polymer material is filled in between the upper tray 100 and the lower tray 200 to obtain a bite registration.

After measuring the jaw relations with the first and second center pieces 101 and 201, the first and second center pieces are connected to their respective extension pieces, including the outer piece 102 and the pair of back pieces 202, such that the assembled upper and lower trays 100 and 200 are used to take the final impression. Thus, according to the present disclosure, a jaw relation record is measured with the first and second center pieces 101 and 201 before the final impression is taken with the complete or assembled upper and lower trays 100 and 200 also including the outer piece 102 and the pair of back pieces 202.

In order to measure the jaw relation record, the mouth of the patient needs to be able to accommodate the trays when they are inserted into the mouth. However, if full-sized trays, such as conventional trays, are inserted into the mouth, it is practically impossible for the patient's mouth to accommodate the full-sized conventional trays because the end portions of the upper and lower trays contact each other at the posterior position of the mouth, thus becoming very bulky in the mouth. In order to solve this problem, the trays of the present invention have been sized to be accommodated in the mouth. For example, the dissembled trays, or a full sized upper tray and the dissembled lower tray, cover at least an anterior position of the mouth while not covering the entire region of the mouth.

Referring to FIGS. 5A-5B, the first and second center pieces 101 and 201 play a role of record base to capture the partial impression intra-orally. Further, the first and second center pieces 101 and 201 also function as a conventional record base to allow the dentist to position the jaw and determine the VD, thus allowing assessment and measurement of the height and position of the jaw. The intra-oral tracer 301 can be adjusted until the patient's mouth is in a clinically acceptable position. From this, the VD can be defined and the CR position can be located. After determining the CR position using the intra-oral tracer 301, the position is captured using PVS (polyvinylsiloxane) material. The first and second center pieces 101 and 201 are then removed from the mouth and each center piece 101 and 201 becomes the positioning guide for the final impression.

The shapes of the trays have unique dimensions, the first center piece 101 providing the position of the tray and the second center piece 201 supporting the borders and capturing muscle movements. The first and second center pieces 101 and 201 may have openings to retain the impression material.

According to another embodiment of the present invention, software is used to obtain a virtual model of the denture to be fabricated. From the scanned data of the PVS impression of the upper and lower trays 100 and 200 and the final impression, a three-dimensional (3-D) model is generated in a computer. The inventive software is used to fabricate dentures by taking the measurements of edentulous regions of the maxilla and mandible from the respective impressions. Further, information on the VD and CR obtained by using the inventive tray assembly is input into the software to create the dentures. The software synthesizes all the data and creates a 3-D model of the edentulous ridge and generates the placement of the teeth and gingival tissue. Included in the software are various sets of teeth types, varying based on shape, size and color. After selecting a desired tooth type, the software automatically generates a denture with the above discussed three reference points to correctly place the teeth. Furthermore, the software corrects any overlap of tooth structure that may arise from a discrepancy between the selected tooth type and the measurements entered from the impressions and gathered data. Once the virtual denture is created, the software will export the file to allow fabrication of the custom denture.

According to yet another embodiment of the present invention, the final denture is milled based on the above described information. Upon receiving the file of the virtual denture generated by the software, a machine will mill an acrylic block into the real denture. The milling denture comprises two different pieces. The first piece is on the teeth portion, and the second piece is on the gingival portion. Each piece is milled separately, and after milling, the two pieces are put together to form the denture.

Alternatively, the denture may be fabricated by rapid prototyping or a combination of the rapid prototyping and a conventional flasking technique. This allows different colors to be used to represent gingival and teeth colors in one operation, using the colors from the rapid prototyping, which are derived from the model.

The present disclosure relates to the art and science of dental prosthetics whereby dental professionals can produce a high quality complete denture at a substantially reduced cost, and in a reduced time, by using newly invented devices and software. It will be apparent to those skilled in the art that various modifications and variations can be made in the present invention without departing from the spirit or scope of the inventions. Thus, it is intended that the present invention covers the modifications and variations of this invention provided they come within the scope of the appended claims and their equivalents.

What is claimed is:

1. A method of measuring jaw relations and obtaining a gum impression of a patient's mouth using a single set of trays comprising a lower tray and an upper tray to fabricate a denture, the method, which allows obtaining the gum impression during a patient's single visit to a dental professional, comprising:
   inserting the lower tray retaining a polymer material and the upper tray retaining the polymer material individually into the patient's mouth to obtain the gum impression comprising a first partial gum impression and a second partial gum impression,
   wherein:
      the lower tray comprises a first piece that is curved at about a central portion to form a right end portion and a left end portion and a pair of second pieces including a right piece that is attached to the right end portion and a left piece that is attached to the left end portion;
      the first piece and the pair of second pieces are configured to be assembled and disassembled;
      the right piece and the left piece are independent pieces that are not coupled to any other element when the right piece and the left piece are not attached to the first piece;
      a size of the lower tray is consistent when the pair of second pieces are attached to the first piece; and
      the upper tray comprises a third piece configured to measure the jaw relations of the patient's mouth along with the first piece of the lower tray and a fourth piece configured to be detachably coupled to the third piece;
   removing the lower tray and the upper tray with the obtained gum impression from the patient's mouth;
   attaching an intra-oral tracer to the first piece removed from the patient's mouth;
   re-inserting the first piece, to which the intra-oral tracer is attached and retaining the first partial gum impression, and the third piece retaining the second partial gum impression together into the patient's mouth;
   measuring the jaw relations by adjusting an adjusting member of the intra-oral tracer that is in contact with a surface of the third piece in the patient's mouth, the first piece retaining the first partial gum impression and the third piece retaining the second partial gum impression during the measurement of the jaw relations;
   filling a gap formed between the first piece of the lower tray and the third piece of the upper tray that are in the patient's mouth with bite registration material, the first piece, to which the intra-oral tracer is attached, retaining the first partial gum impression and the third piece retaining the second partial gum impression while the gap is filled with the bite registration material; and
   removing the first piece, to which the intra-oral tracer is attached and retaining the first partial gum impression, and the third piece retaining the second partial gum impression, the bite registration material filled between the first piece and the third piece, from the patient's mouth.

2. The method of claim 1, further comprising:
scanning the gum impression and fabricating the denture using software processed in a computer based upon a scanned image of the gum impression.

3. The method of claim 2, further comprising:
generating a virtual model of the denture using the software; and
virtually combining imported three-dimensional images of the patient's soft tissue of the mouth and new three-dimensional images that represent teeth.

4. The method of claim 3, further comprising:
importing and displaying multiple three-dimensional images using the software;
manipulating the multiple three-dimensional images to locate the new three-dimensional images that represent teeth to a proper relative location in the patient's mouth; and
selecting desired types of teeth, molars, and incisors and resizing the selected teeth, molars, and incisors to fit appropriately on the three-dimensional images of the soft tissue.

5. The method of claim 1, wherein the third piece is sized to cover the patient's upper anterior gum and has a front portion and a rear portion.

6. The method of claim 5, wherein the fourth piece is further configured to be detachably coupled to the rear portion of the third piece.

7. The method of claim 1, wherein the pair of second pieces are configured to fit over the patient's gum when the pair of second pieces are coupled to the first piece.

8. The method of claim 1, wherein the jaw relations comprise a vertical dimension and a centric relation.

9. The method of claim 1, wherein the adjusting member comprises a screw.

10. The method of claim 1, wherein the adjusting member is adjusted by being raised or lowered such that a distance between the first piece and the third piece is changed according to the adjustment.

11. The method of claim 1, wherein the first piece of the lower tray is sized to cover an anterior portion of the patient's lower gum and the pair of second pieces are sized to cover distal portions or the rest of the lower gum when attached to the first piece and the entire lower tray is inserted into the patient's mouth.

12. The method of claim 1, wherein the single set of trays is made of plastic.

13. The method of claim 1, wherein the first piece comprises a receiving structure configured to receive the intra-oral tracer.

14. The method of claim 1, wherein the intra-oral tracer is shaped to define a hole and the adjustable member is inserted into the hole to be raised or lowered through the hole.

15. The method of claim 1, wherein the first piece of the lower tray with the intra-oral tracer attached and the third piece of the upper tray are sized and configured to be inserted together into the mouth to determine the jaw relations.

16. The method of claim 1, wherein a size of the lower tray including the first piece and the pair of second pieces and a size of the upper tray including the third piece and the fourth piece are fixed.

17. The method of claim 1, wherein the intra-oral tracer is coupled to the first piece such that an open space between the right end portion and the left end portion is substantially covered by the intra-oral tracer.

* * * * *